United States Patent [19]

Euwer

[11] Patent Number: Plant 6,194

[45] Date of Patent: Jun. 7, 1988

[54] COLUMBIA RED ANJOU PEAR TREE

[76] Inventor: Eugene C. Euwer, 8469 Cooper Spur Rd., Parkdale, Oreg. 97041

[21] Appl. No.: 846,358

[22] Filed: Mar. 31, 1986

[51] Int. Cl.[4] ..... A01H 5/03

[52] U.S. Cl. ..... Plt./36

[58] Field of Search ..... Plt. 36

*Primary Examiner*—Robert E. Bagwill

*Attorney, Agent, or Firm*—Chernoff, Vilhauer, McClung & Stenzel

[57] ABSTRACT

A pear tree which is a mutation of the standard Anjou variety, characterized by an overall bright-red fruit skin color and by a slow respiration rate and low ethylene production of the fruits during storage. The slower fruit ripening rate which results from these storage characteristics imparts to the fruit a longer storage and shelf life when compared with fruits harvested from the standard Anjou parent and those harvested from another patented Red Anjou sport variety.

4 Drawing Sheets

BACKGROUND AND SUMMARY OF THE INVENTION

This invention relates to a new and distinct variety of pear tree, and more particularly to a sport of the pear tree commonly known as the Anjou or Beurre d'Anjou.

The original specimen of this new variety of pear was discovered by the inventor as a sport spur twig, in the month of September 1976, in his orchard located on O'Leary Road, in the Dee Flat area of Hood River Valley, Oreg. On the sport spur twig, which was growing in the very top portion of a 60-year-old Beurre d'Anjou pear tree, was a single bright-red fruit which was distinctly different from the green-colored standard Anjou pear fruits borne on the rest of the tree. In succeeding years this small spur twig grew into a sport limb which continued to bear bright-red fruits identical to the original single fruit.

Immediate steps were taken to preserve and to further test the newly discovered sport variety. The newly discovered sport was first asexually reproduced by the inventor in 1979, by grafting. Scions of the new sport limb were placed on pear seedlings and clonal rootstocks, and second generation trees were propagated and planted, to see if the overall bright-red coloring characteristic of the fruit would be transmitted through asexual reproduction to succeeding generations of trees. In the years following discovery of the sport limb, several older pear trees located at Parkdale, Oreg., and at Parker, Wash., were topworked with scion wood from it.

All second generation trees now in bearing have illustrated that the distinctive overall bright-red coloring characteristic of the fruits is established and has been transmitted to successive generations by asexual propagation of the newly discovered pear tree.

Additional tests were conducted to see if other characteristics of the newly discovered sport were different from the corresponding characteristics of fruits harvested from standard Anjou trees and from another known sport of the common Anjou, the Red Anjou which is the subject of Gebhard U.S. Plant Pat. No. 1,992.

BRIEF DESCRIPTION OF THE DRAWINGS

FIG. 4 is a photographic representation of a typical fruit of the new variety, together with a typical fruit of the red Anjou disclosed in U.S. Plant Pat. No. 1,992.

FIG. 5 is a photographic representation of a typical leaf specimen of the new pear tree, along with a typical leaf of the parent Anjou pear tree.

DETAILED DESCRIPTION OF THE INVENTION

Figure 1:
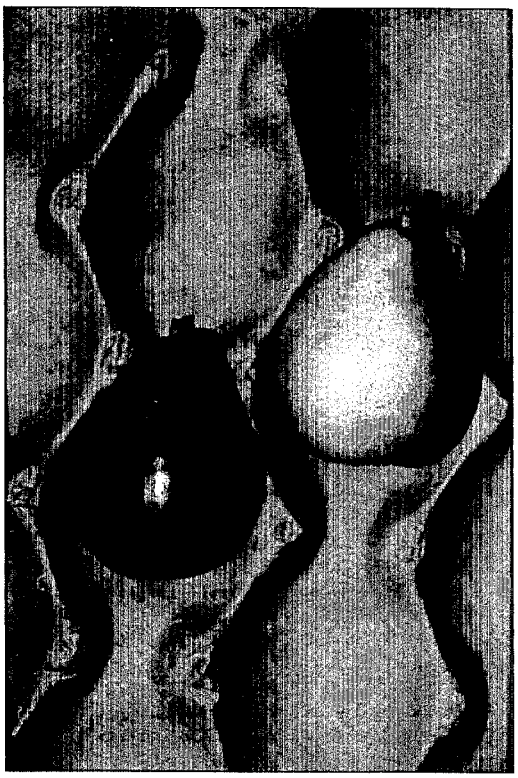
FIG. 1 is a photographic representation of a typical specimen of the fruit of the pear tree of the present invention, particularly showing the overall bright-red skin color of the fruit in comparison to the fruit of its parent, the common Anjou, also shown in FIG. 1.

Referring now to the drawings, in FIG. 1 it may be seen that the fruit of the new variety of pear tree, which has been named Columbia Red Anjou, has an overall bright-red skin color, although the fruit of the parent Anjou variety has a green skin color. The shape of the fruit of the new variety of pear tree is oblong-obovate-pyriform, similar to that of the parent Anjou pear.

Figure 2:
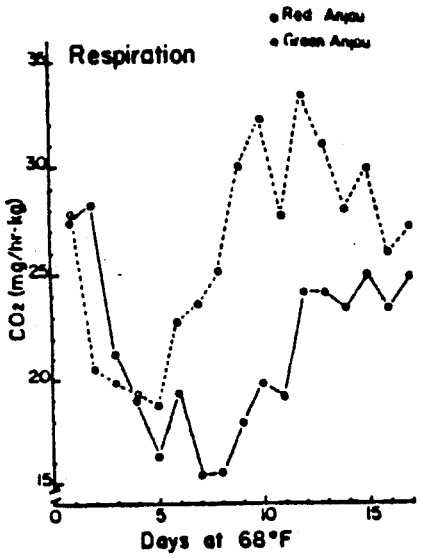
FIG. 2 is a graph showing the respiration rate of the fruit of the new pear tree of the present invention in comparison with that of the parent Anjou variety under similar storage conditions, as measured by production of carbon dioxide by the stored fruits, with the solid dot data points indicating observations of the new pear variety and the open circle data points indicating observations of the parent Anjou variety.
Figure 3:
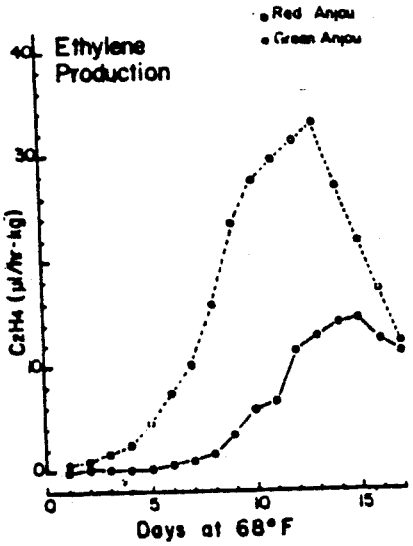
FIG. 3 is a graph showing the ripening rate of the fruit of the new pear tree of the present invention in comparison with that of the parent Anjou variety under similar storage conditions, as measured by production of ethylene by the stored fruits, with the solid dot data points indicating observations of the red Anjou fruits of the present invention and the open circle data points indicating observations of the parent Anjou fruits.

Referring to FIG. 2, results of post-harvest storage and fruit quality tests which were conducted at the Mid-Columbia Experiment Station, in Hood River, Oreg., show that fruits of the pear tree of the invention have a lower rate of respiration than the fruit of the parent Beurre d'Anjou pear tree. Similarly, the rate of ethylene production is lower for the newly discovered pear tree, as may be seen from FIG. 3. Since respiration and ethylene production rates are direct indications of the rate of ripening activity of pear fruits, the lower rates of respiration and ethylene production of the Columbia Red Anjou fruits indicate a longer storage and shelf-life than the standard Anjou pear fruits harvested from the same tree and stored under similar conditions. These results show that fruits of the newly discovered pear variety harvested from the same parent tree as the standard Anjou fruits are not physiologically identical.

Table 1, below, shows that unripened fruit from the newly discovered Columbia Red Anjou has a higher content of titratable acids and soluble solids than fruits of either the parent green Anjou or the previously mentioned Red Anjou shown in Gebhard U.S. Plant Pat. No. 1,992. High titratable acid and soluble solid contents in Anjou pear fruits are associated with good storage life and high dessert quality of the fruits.

TABLE 1

| Type of Fruit | Fruit Firmness (lb) | Titratable Acids (meq/100 ml juice) | Soluble Solids % |
|---|---|---|---|
| Columbia Red d'Anjou | 14.0 | 5.4 | 13.5 |
| Gebhard Red d'Anjou (P.P. 1992) | 12.7 | 3.2 | 12.1 |
| Green d'Anjou | 14.4 | 3.9 | 12.3 |

Fruit conditions of unripened red and green d'Anjou Pears stored at 30° F. until December 6, 1982.

The fruits of the newly discovered pear tree have firmness which was found to be similar to that of the Anjou parent, but the fruit pressure tested approximately 1 to 1½ pounds greater than the fruits of the Red Anjou pear described in U.S. Plant Pat. No. 1,992.

Other factors brought out by the storage and fruit quality tests conducted show that fruit texture and the juiciness of the Columbia Red Anjou were slightly higher than the Gebhard Red Anjou of U.S. Plant Pat. No. 1,992, and that the newly discovered pear tree's fruit also had a noticeably higher distinct flavor rating, as may be seen from Table 2. These Organoleptic (taste) tests were conducted to determine dessert quality and were based on scores of 1 through 5 by a panel of nine participants. The dessert quality of ripened fruit was evaluated by the following three categories including texture, juiciness and flavor. Each category was further divided into five ratings. For texture: buttery=5, moderately buttery=4, slightly buttery=3, moderately coarse or mealy=2, and coarse or mealy=1. For juiciness: juicy=5, moderately juicy=4, slightly juicy=3, moderately dry=2, and dry=1. For flavor: excellent=5, good=4, fair=3, poor=2, and unacceptable=1. The mean scores according to this scheme of evaluation are shown in Table 2.

TABLE 2

Organoleptic Evaluation of the Dessert Quality of Ripened Red d'Anjou Fruits.

| Type of Fruits | Quality Ratings (Scores) | | |
|---|---|---|---|
| | Texture | Juiciness | Flavor |
| Columbia Red d'Anjou | 3.7 | 4.4 | 4.0 |
| Gebhard Red d'Anjou (P.P. 1992) | 2.7 | 3.6 | 3.0 |

Since the reduction of extractable juice between unripened and ripened fruits is inversely related to the texture and juiciness of ripened fruit, the test results displayed in Table 3 show that the fruits of the new Columbia Red Anjou pear, with its higher amount of net reduction of extractable juice possess a higher dessert quality than those pear selections compared to it in Table 3.

TABLE 3

Changes in Extractable Juice Between Unripened and Ripened d'Anjou Fruits.

| Type of Fruit | Extractable Juice (ml/100 g F.W.) | | |
|---|---|---|---|
| | Unripened Fruit | Ripened Fruit | Net Reduction |
| Columbia Red d'Anjou | 72 | 61 | 11 |
| Gebhard Red d'Anjou (P.P. 1992) | 73 | 63 | 10 |
| Green d'Anjou | 72 | 63 | 9 |

Other visible differences noted when the new Columbia Red Anjou pear was compared to the previously patented Gebhard strain of Red Anjou pear tree are as follows:

1. Fruits harvested from the new pear tree typically possess an oblong-obovate-pyriform shape with slightly unequal sides. This shape is more typical of the common Anjou than of the Gebhard strain of Red Anjou. Fruits of the Gebhard strain possess a rounder, less pyriform shape, with their sides more equal in appearance, as may be seen in FIG. 4.

2. Fruit dots appear smaller in the new pear tree's fruits than in the fruits of the other Red Anjou pear.

3. The fruits of the new Columbia Red Anjou pear have a slightly thinner skin than that of the Gebhard strain of Red Anjou.

4. The fruit of the newly discovered pear tree appears to have slightly less red color prior to picking time, but finally ripens off with an overall, attractive, bright-red color when the fruits are ready for harvest.

Figure 6:
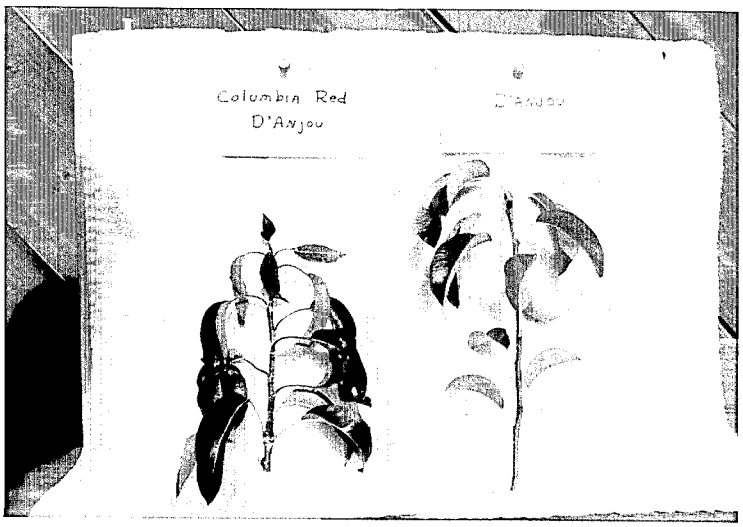
FIG. 6 is a photographic representation of a branch of the new pear tree of the present invention, alongside a similar branch of the parent Anjou variety, showing the darker foliage and bark of the pear tree of the new invention.
Figure 7:
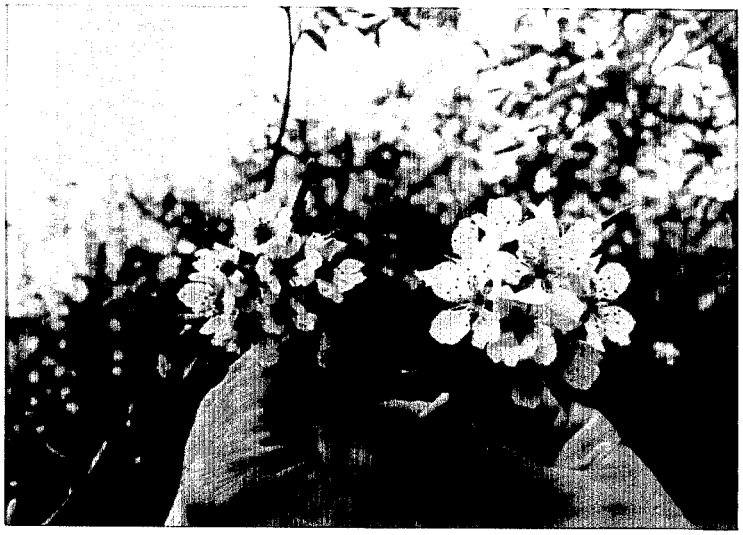
FIG. 7 is a photographic view showing typical flowers of the new pear tree variety, alongside flowers of the parent Anjou variety of pear tree.

In several external particulars, the new pear tree is similar to the standard Anjou variety, in that the pear fruits have a shape and flesh color similar to those of the parent Anjou. The new pear tree's overall tree characteristics are also similar to the Anjou parent, except for darker leaves (FIG. 6) and the darker and striped pink color of the petals and pedicels of the flowers of the new variety (FIG. 7). Tree size, shape, and growth characteristics of the new tree are similar to those of the Anjou parent.

The following detailed description of the new Columbia Red Anjou variety of pear tree is based upon observations of pear specimens made with reference to botanical authorities. Except where common terms of color definition are employed, all major colors are described with reference to the Munsell Color Cascade chart.

Parentage: Limb sport of Anjou (Beurre d'Anjou).

Locality of observations: Parkdale, Org. and Parker, Wash.

Tree:

*Size.*—Large.

*Vigor.*—Vigorous.

*Form.*—Spreading.

*Growth.*—Moderate.

*Hardiness.*—Hardy.

*Production.*—Very productive.

*Bearing.*—Late, slightly irregular.

Trunk:

*Form.*—Straight.

*Size.*—Stocky.

*Texture.*—Smooth.

Branches:

*Main branches.*—Stocky, spreading, thick, strong.

*Lateral branches.*—Slightly zigzag, covered with gray scarf-skin over reddish-brown few small lenticels.

*Branchlets.*—Long with long internodes, smooth, glabrous, reddish-brown with slight green tinge.

*Lenticels.*—Many, conspicuous, raised.

Leaves:

*Size.*—Medium, average length 3 to 3½", average width 1½ to 1¾".

*Form.*—Elongated, oval.

*Apex.*—Taper, pointed.

*Thickness.*—Thin.

*Pubescence.*—None.

*Texture.*—Leathery, smooth.

*Margin.*—Nearly entire, crenate.

*Petiole.*—Medium-thick, average length 1½ to 2".

*Color.*—Topside dark green 22-14), underside lighter green (23-13).

Leaf-buds:

*Form.*—Small, short, obtuse, nearly free.

Leaf-scars: Prominent.

Flowers:

*Blooming period.*—In Parker, Wash. about April 12 to April 19, in Dee, Oreg. about April 17 to April 24.

*Size.*—Large, average diameter 1⅜ to 1½".

*Color.*—Very light pink with darker pink streaks (41-4), very showy, in dense clusters.

Petals:

*Shape.*—Obovate, broad.

*Color.*—Very light pink with darker pink streaks (41-4).

*Pedicels.*—Pubescent, reddish, very thick, ½ to ¾" long.

*Fertility.*—Fertile but crops best with cross-pollination.

Flower buds:

*Size.*—Large.

*Shape.*—Conical, long, plump, free.

Fruit:

*Date of first picking.*—In Parker, Wash. about August 28, in Dee, Oreg. about September 15.

*Date of last picking.*—In Parker, Wash. about September 2, in Dee, Oreg. about September 22.

*Retention.*—Hangs well.

*Size.*—Large, uniform, average length 3½ to 3¾", average width 2½ to 3".

*Form.*—Oblong, obovate, pyriform, irregular surface outline, sides slightly unequal, uniform.

*Stem.*—Woody, very thick, short, average length ½ to ¾".

*Cavity.*—Obtuse, shallow, slightly russeted and furrowed, usually lipped.

*Calyx.*—Open, small.

*Lobes.*—Long, narrow, acuminate, separated at base.

*Basin.*—Shallow, narrow, obtuse, smooth, symmetrical, regular.

Skin:

*Texture.*—Smooth, tender, thin.

*Color.*—Bright-red (38-14), slight russet at basin, occasional fine russet lines and markings.

*Dots.*—Many, small, russet, conspicuous.

Flesh:

*Color.*—Yellowish-white (25-1).

*Texture.*—Slightly granular, firm, tender, buttery, juicy.

*Flavor.*—Sweet, spicy, rich, aromatic.

*Eating quality.*—Good when properly ripened.

*Core.*—Large, closed.

*Core lines.*—Clasping.

*Calyx-tube.*—Short, wide, conical.

Seed:

*Size.*—Large.

*Shape.* —Wide, long, plump, acuminate, tufted at tips.

*Color.*—Dark brown (28-15).

Use: Market, dessert, shipping.

Keeping quality: Excellent.

Shipping quality: Excellent.

Resistance to insects and diseases: Similar to standard Anjou, fairly free from blight, resistant to scab and mildew, medium resistance to usual pear insect pests.

The newly discovered pear tree as described herein may vary in detail slightly as a result of differences in climatic and soil conditions under which pear trees of the new variety are grown. The above description is based upon specimens of the newly discovered pear tree grown in Oregon's Hood River Valley and in the Yakima Valley of Washington.

What is claimed is:

1. A new and distinct variety of pear tree substantially as illustrated and described herein, characterized particularly by the overall bright-red skin color of the fruit, the slower respiration rate and lower ethylene production of the stored fruits, its slower fruit-ripening rates and longer storage and shelf-life than in the parent Anjou variety of pear tree, and its fruit having an oblong-obovate-pyriform shape, many conspicuous small russet fruit dots, a thin skin, red color prior to harvest, sweet spicy flesh and slightly granular, firm, tender, buttery, and juicy texture, and its flowers having a very light pink coloration with streaks of darker pink.

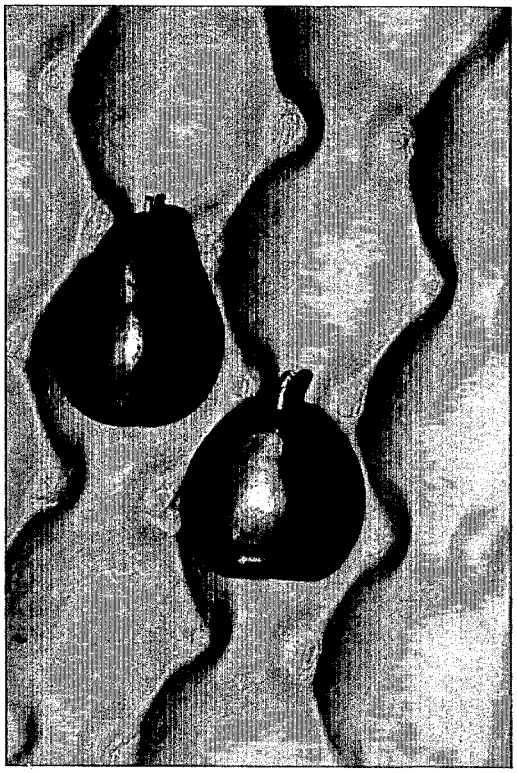
FIG. 4
FIG. 5
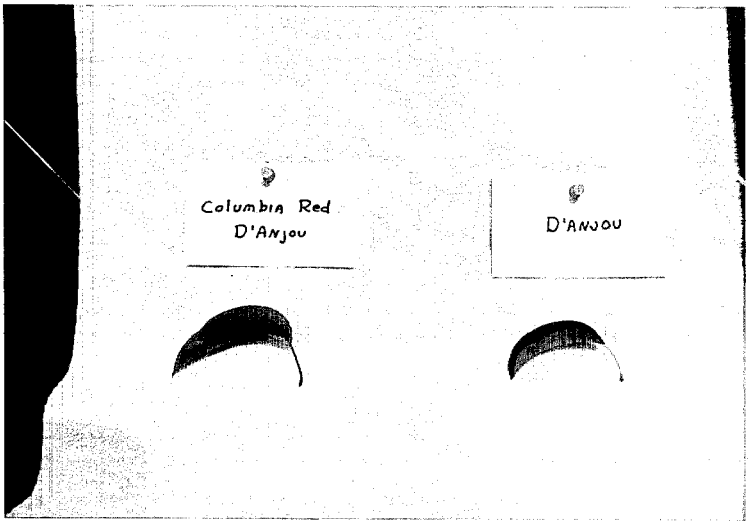

* * * * *